United States Patent [19]

Rivier et al.

[11] Patent Number: 5,064,939

[45] Date of Patent: Nov. 12, 1991

[54] CYCLIC GNRH ANTAGONISTS

[75] Inventors: Jean E. F. Rivier, La Jolla; Steven C. Koerber, Encinitas; Arnold T. Hagler, La Jolla; Catherine L. Rivier, La Jolla; Wylie W. Vale, Jr., La Jolla, all of Calif.

[73] Assignee: The Salk Institute for Biological Studies, San Diego, Calif.

[21] Appl. No.: 475,767

[22] Filed: Feb. 6, 1990

[51] Int. Cl.$^5$ .................... A61K 37/00; A61K 37/38; C07K 5/12; C07K 7/20
[52] U.S. Cl. .................................... 530/317; 530/311
[58] Field of Search ................... 514/9, 10, 17, 15; 530/311, 317

[56] References Cited

U.S. PATENT DOCUMENTS

| | | | |
|---|---|---|---|
| 4,161,521 | 7/1979 | Verber et al. | 424/177 |
| 4,191,754 | 3/1980 | Veber et al. | 424/177 |
| 4,565,804 | 1/1986 | Rivier et al. | 514/15 |
| 4,569,927 | 2/1986 | Rivier et al. | 514/15 |
| 4,611,054 | 9/1986 | Freidinger | 530/311 |
| 4,619,914 | 10/1986 | Vale, Jr. et al. | 514/15 |
| 4,628,044 | 12/1986 | Loozen | 514/15 |
| 4,652,550 | 3/1987 | Rivier et al. | 514/15 |
| 4,659,691 | 4/1987 | Veber et al. | 514/11 |
| 4,661,472 | 4/1987 | Rivier et al. | 514/15 |
| 4,690,916 | 9/1987 | Nestor, Jr. et al. | 514/15 |
| 4,703,106 | 10/1987 | Hirose et al. | 530/307 |
| 4,740,500 | 4/1988 | Vale, Jr. et al. | 514/15 |
| 4,801,577 | 1/1989 | Nestor, Jr. et al. | 514/15 |

OTHER PUBLICATIONS

Nestor et al., "Design of Luteinizing Hormone Releasing Hormone Antagonists with Reduced Potential for Side Effects", *Peptides* 1988, 592–594.

*Eleventh American Peptide Symposium*, The Salk Institute and University of California, San Diego, La Jolla, CA., Jul. 9–14, 1989: Abstract LT7.

*Third Symposium of the Protein Society*, Seattle, WA., Jul. 29–Aug. 2, 1989: Abstract re Design of GnRH Antagonists.

*Primary Examiner*—Lester L. Lee
*Assistant Examiner*—Avis Davenport
*Attorney, Agent, or Firm*—Fitch, Even, Tabin & Flannery

[57] ABSTRACT

Peptides which inhibit the secretion of gonadotropins by the pituitary gland and inhibit the release of steroids by the gonads. Administration of an effective amount of such GnRH antagonists prevents ovulation of female mammalian eggs and/or the release of steroids by the gonads. These peptides may be used to treat steroid-dependent tumors, such as prostatic and mammary tumors. The peptides include cyclic, bicyclic and tricyclic analogs of the decapeptide GnRH, and preferably there are at least two covalent bonds between the residues in the 4- and 10-positions, the residues in the 5- and 8-positions and the residues in the 1- and 3-positions, respectively. Examples of such bonds include a disulfide linkage between Cys residues, an amide linkage between a side chain amino group and a side chain carboyxl group, a dicarba linkage between side-chain alkyl groups, and a carba linkage between a side-chain alkyl group and a side-chain sulfhydryl group.

35 Claims, No Drawings

1

CYCLIC GNRH ANTAGONISTS

This invention was made with Government support under Grant HD-02903-B awarded by the National Institutes of Health (DHHS). The Government has certain rights in this invention.

The present invention relates to peptides which inhibit the release of gonadotropins by the pituitary gland in mammalians, including humans, and to methods of preventing ovulation and/or inhibiting the release of steroids More particularly, the present invention is directed to peptides which inhibit gonadal function and the release of the steroidal hormones, progesterone and testosterone.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and they also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as GnRH although it has also been referred to as LH-RH and as LRF. GnRH has been isolated and characterized as a decapeptide having the following structure:

pGlu-His-Trp-Ser-Tyr-Gly-Leu-Arg-Pro-Gly-NH$_2$

Peptides are compounds which contain two or more amino acids in which the carboxyl group of one acid is linked to the amino group of the other acid. The formula for GnRH, as represented above, is in accordance with conventional representation of peptides where the amino terminus appears to the left and the carboxyl terminus to the right The position of the amino acid residue is identified by numbering the amino acid residues from left to right. In the case of GnRH, the hydroxyl portion of the carboxyl group of glycine at the C-terminus has been replaced with an amino group(NH$_2$). The abbreviations for the common individual amino acid residues are conventional and are based on the trivial name of the amino acid, e.g. Pglu is pyroglutamic acid, Glu is glutamic acid, His is histidine, Trp is tryptophan, Ser is serine, Tyr is tyrosine, Gly is glycine, Leu is leucine, Nle is norleucine, Orn is ornithine, Arg is arginine, Pro is proline, Sar is sarcosine, Phe is phenylalanine, Ala is alanine, Val is valine, Nva is norvaline, Ile is isoleucine, Thr is threonine, Lys is lysine, Asp is aspartic acid, Asn is asparagine, Gln is glutamine, Cys is cysteine, and Met is methionine. Except for glycine, the amino acids which appear in the peptides of the invention are of the L-configuration unless noted otherwise.

There are reasons for desiring to prevent ovulation in female mammalians, and the administration of GnRH analogs that are antagonistic to the normal function of GnRH have been used to suppress or delay ovulation. For this reason, analogs of GnRH which are antagonistic to GnRH are being investigated for their potential use as a contraceptive or for regulating conception periods. GnRH antagonists may also be used for the treatment of precocious puberty and endometriosis. Such antagonists have also been found useful to regulate the secretion of gonadotropins in male mammals and can be employed to arrest spermatogenesis, e.g. as male contraceptives, and for treatment of prostatic hypertrophy. More specifically, GnRH antagonists can be used to treat steroid-dependent tumors, such as prostatic, brain and mammary tumors.

It is desired to provide improved peptides which are strongly antagonistic to endogenous GnRH and which prevent secretion of LH and the release of steroids by the gonads of mammals, and to also provide compounds which are biologically effective in vivo when administered orally.

SUMMARY OF THE INVENTION

The present invention provides peptides which inhibit the release of gonadotropins in mammalians, including humans, and it also provides methods for inhibiting the release of steroids by the gonads of male and female mammalians. The improved GnRH analogs are strongly antagonistic to GnRH and have an inhibitory effect on the reproduction processes of mammalians; thus, they are referred to as GnRH antagonists. These analogs may be used to inhibit the production of gonadotropins and sex hormones under various circumstances, including precocious puberty, hormone dependent neoplasia, dysmenorrhea, endometriosis and steroid-dependent tumors.

Generally, in accordance with the present invention, peptides have been synthesized which strongly inhibit the secretion of gonadotropins by the pituitary gland of mammalians, including humans, and/or inhibit the release of steroids by the gonads. These peptides are cyclic, and are preferably bicyclic or tricyclic analogs of GnRH wherein there are at least two covalent bonds, i.e., between the following pairs of residues: the 4-position residue and the 10-position residue, the 5-position residue and the 8-position residue and the 1-position residue and the 3-position residue. Certain bicyclic peptides which do not have a covalent bond between the 1- and 3-position residues should have a 1-position substitution, preferably dehydroPro or β-(1-or 2-naphthyl)-D-alanine(hereinafter β-D-1NAL or β-D-2NAL) and a 3-position substitution, preferably in the form of unsubstituted or substituted D-Trp, D-3PAL, β-D-2NAL or β-D-1NAL. All of the peptides preferably have a 2-position substitution in the form of a modified D-Phe residue. The 4-position substitution may be Cys, a diamino acid having not more than 5 carbon atoms, a dicarboxyl amino acid, such as Asp or Glu, or Abu. The 5-position is preferably occupied by Glu and the 8-position by Lys when these two residues are covalently bonded; however, optionally the following residues can be employed in these positions: homoglutamic acid (Hgl); homohomoglutamic acid (Hhg), i.e., 1,7-dicarboxy, 2-amino, heptanoic acid; homolysine (Hly) and homohomolysine (Hhl) or 1-carboxy, 2,8-diamino, octanoic acid. The peptide also has a 6-position substitution, can have an optional substitution in the 7-position, such as Nle, NML, Phe, Nva, Met, Tyr, Trp or PAL, and can have an optional modification of Pro in the 9-position. The substitution in the 10-position is complementary to the 4-position residue. For the tricyclic compounds and certain of the bicyclic compounds, the residues in the 1- and 3-positions are complementary, as generally set forth with respect to those in the 4- and 10-positions; however, it may be preferred to employ a dicarba bond between these two residues of a length longer than that provided by a pair of Abu residues.

Modified D-Phe in the 2-position provides increased antagonistic activity as a result of the specific modifications present in the benzene ring. Single substitutions for hydrogen in the ring are preferably made in the para- or 4-position, but might instead be in either the 2- or 3-position; the substitutions are selected from chloro, fluoro, bromo, methyl, methoxy and nitro, with chloro, fluoro and nitro being preferred. Dichloro substitutions are in the 2,4 or 3,4 positions in the ring. The alpha-carbon atom may also be methylated, e.g. $(C^aMe/4Cl)$Phe. The 1-position substituent is preferably modified so that its alpha amino group contains an acyl group, such as formyl(For), acetyl(Ac), acrylyl(Acr), vinylacetyl(Vac) or benzoyl(Bz), with acetyl and acrylyl being preferred. PAL and D-PAL represent the L- and D-isomers of pyridylalanine where the $\beta$-carbon of Ala is linked to the 2-, 3- or 4-position, preferably to the 3-position, on the pyridine ring. When $\beta$-D-NAL is present in the 1-position, a hydrophillic D-amino acid residue, such as 4NH$_2$-D-Phe, 4-guanidino-D-Phe, D-His, D-Arg, D-Har(Homoarginine) or D-PAL is preferably present in the 6-position. When dehydroPro is present in the 1-position, a D-isomer of a lipophilic amino acid, such as D-Trp, D-Phe, For-D-Trp, NO$_2$-D-Trp, D-Leu, D-Ile, D-Nle, D-Tyr, D-Val, D-Ala, D-Ser-(OtBu), $\beta$-D-NAL or (imBzl)D-His is preferably in the 6-position, but D-PAL may be used.

These GnRH antagonists are active when administered orally compared to previously available GnRH antagonists. The peptides inhibit ovulation of female mammals when administered at low levels at proestrus and are also effective to cause resorption of fertilized eggs if administered shortly after conception. These peptides are also effective for the contraceptive treatment of male mammals and for the treatment of steroid-dependent and other tumors.

DETAILED DESCRIPTION OF THE PREFERRED EMBODIMENTS

More specifically, certain preferred bicyclic peptides of the present invention are represented by the following Formula I:

D-Nva; A' is A, NH$_2$, NHCH$_3$ or gua; C is H, imBzl or dinitrophenol; D is H or di-lower alkyl; R$_7$ is Nle, Leu, NML, Phe, Met, Nva, Tyr, Trp or PAL; E is H, OH or dehydro and R$_{10}$ is Cys, Asp, Glu, Orn, Dbu, Dpr or Abu; provided however that when R$_4$ is Cys or Abu, R$_{10}$ is Cys or Abu; when R$_4$ is Asp or Glu, R$_{10}$ is Orn, Dbu or Dpr; and when R$_4$ is Orn, Dbu or Dpr, R$_{10}$ is Asp or Glu. When R$_1$ is $\beta$-D-NAL, then R$_6$ is preferably 4-NH$_2$-D-Phe, D-Har, D-His, 4-gua-D-Phe, D-PAL or D-Arg. As indicated hereinbefore, Hgl and Hhg can be substituted for Glu in the 5-position, and Hly or Hhl can be substituted for Lys in the 8-position.

By dehydroPro is meant 3,4 dehydroproline, $C_5H_7O_2N$. By $\beta$-D-NAL is meant the D-isomer of alanine which is substituted by naphthyl on the $\beta$-carbon atom, i.e., also 3-D-NAL. Preferably $\beta$-D-2NAL is employed, the attachment to naphthalene is at the 2-position on the ring structure; however, $\beta$-D-1NAL may also be used. PAL represents alanine which is substituted by pyridyl on the $\beta$-carbon atom; preferably the linkage is to the 3-position on the pyridine ring. When substituted D-Trp is employed, single substitutions for hydrogen may be made in either the 5- or 6-position, which are selected from chloro, fluoro, bromo, methyl, amino, methoxy and nitro, with chloro, fluoro and nitro being preferred. Alternatively, the indole nitrogen may be acylated, e.g. with formyl (N$^{in}$-For- or 1For-) or with acetyl. N$^{in}$For-D-Trp and 6NO$_2$-D-Trp are the preferred substituted residues. When either D-Arg or D-Har is present in the 6-position, or Arg is present in the 8-position, the guanidino side chain can be di-substituted with lower alkyl(C$_1$ to C$_4$), preferably diethyl. By NML is meant N$^a$CH$_3$-L-Leu. By Abu is meant 2-aminobutyric acid and by Dbu is meant 2,4-diaminobutyric acid. By Dpr is meant 2,3-diaminopropionic acid. When dehydroPro is present in the 1-position, a lipophilic residue is preferably in the 6-position. By 4-gua-D-Phe is meant a residue of D-Phe having a guanidino group substituted in the para-position.

Other biologically active monocyclic and bicyclic peptides can be fashioned which have a covalent bond between the residues in the 1- and 3-positions and may optionally have such a bond between the residues in the 4- and 10-positions or between the residues in the 5- and 8-positions. Such peptides may have the following formula, with the understanding that there would be a cyclizing covalent bond between residues R$_1$ and R$_3$, and optionally one between R$_5$ and R$_8$, or between R$_4$

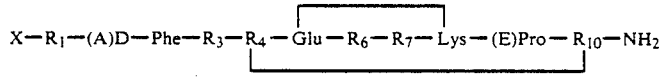

wherein X is hydrogen or an acyl group having 7 or less carbon atoms; R$_1$ is dehydroPro, D-pGlu, (A)D-Phe, (B)D-Trp, Pro, or $\beta$-D-NAL; A is H, Cl, F, NO$_2$, CH$_3$, OCH$_3$, $C^aMe/4Cl$, Cl$_2$ or Br; B is H, NO$_2$, NH$_2$, OCH$_3$, F, Cl, Br, CH$_3$, N$^{in}$For or N$^{in}$Ac; R$_3$ is D-PAL, $\beta$-D-NAL or (B)D-Trp; R$_4$ is Cys, Asp, Glu, Orn, Dbu, Dpr or Abu; R$_6$ is $\beta$-D-NAL, (B)D-Trp, (A')D-Phe, (D)D-Har, D-Tyr, (C)D-His, D-PAL, (D)D-Arg, D-Leu, D-Ile, D-Val, D-Nle, D-Ala, D-Pro, D-Ser(OtBu) or and R$_{10}$:

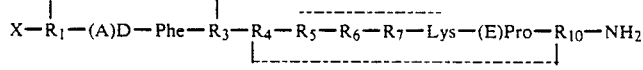

wherein X is hydrogen or an acyl group having 7 or less carbon atoms; R$_1$ is D-Cys, D-Abu, asp, glu, hgl, hhg, lys, hly, hhl, orn, dbu or dpr; A is H,Cl, F, NO$_2$, CH$_3$, OCH$_3$, $C^aMe/4Cl$, Cl$_2$ or Br; R$_3$ is D-Cys, abu, asp, glu, hgl, hhg, lys, hly, hhl, orn, dbu or dpr; R$_4$ is Ser, Cys, Asp, Glu, Orn, Dbu, Dpr or Abu; R$_5$ is Tyr or Glu; R$_6$ is $\beta$-D-NAL, (B)D-Trp, (A')D-Phe, (D)D-Har, D-Tyr, (C)D-His, D-PAL, (D)D-Arg, D-Leu, D-Ile, D-Val, D-Nle, D-Ala, D-Pro, D-Ser(OtBu), or D-Nva; A' is A, NH$_2$, NHCH$_3$ or gua; B is H, NO$_2$, NH$_2$, OCH$_3$, F, Cl, Br, CH$_3$, N$^{in}$For or N$^{in}$Ac; C is H, imBzl or dinitrophenol; D is H or di-lower alkyl; R$_7$ is Nle, Leu, NML, Phe, Met, Nva, Tyr, Trp or PAL; E is H, OH or dehydro; R$_8$ is (D)Arg, (D)Har or Lys and R$_{10}$ is Gly, D-Ala, Cys, Asp, Glu, Orn, Dbu, Dpr or Abu; provided however that when R$_4$ is Cys or Abu, R$_{10}$ is Cys or Abu; when R$_4$ is Asp or Glu, R$_{10}$ is Orn, Dbu or Dpr; when R$_4$ is Orn, Dbu or Dpr, R$_{10}$ is Asp or Glu; when R$_5$ is Glu, R$_8$ is Lys; and provided further that when R$_1$ is D-Cys or D-Abu, R$_3$ is D-Cys or D-Abu; when R$_1$ is asp, glu, hgl or hhg, R$_3$ is lys, hly, hhl, orn, dbu or dpr; and when R$_1$ is lys, hly, hhl, orn, dbu or dpr, R$_3$ is asp, glu, hgl or hhg. By the lower case designation, e.g. asp, is meant that the residue may be either the L- or the D-isomer, i.e. L-Asp or D-Asp; however, the D-isomers are preferred in both the 1- and 3-positions.

In certain preferred tricyclic peptides, the formula is generally as set forth above except that R$_1$ is D-Cys, D-Abu, D-Asp, D-Glu, D-Hgl, D-Hhg, D-Lys, D-Hly, D-Hhl, D-Orn, D-Dbu or D-Dpr and R$_3$ is a complementary residue selected from the same group; however, in the tricyclic peptides at least 2 of the 3 cyclizing bonds should preferably be amide and/or dicarba bonds. The following formula is representative of certain particularly preferred tricyclic peptides:

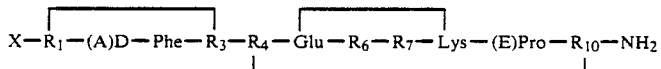

wherein X is hydrogen or an acyl group having 7 or less carbon atoms; R$_1$ is D-Cys, D-Abu, D-Asp, D-Glu, D-Hgl, D-Hhg, D-Lys, D-Hly, D-Hhl, D-Orn, D-Dbu or D-Dpr; A is H, Cl, F, NO$_2$, CH$_3$, OCH$_3$, C$^a$Me/4Cl, Cl$_2$ or Br; R$_3$ is D-Cys, D-Abu, D-Asp, D-Glu, D-Hgl, D-Hhg, D-Lys, D-Hly, D-Hhl, D-Orn, D-Dbu or D-Dpr; R$_4$ is Cys, Asp, Glu, Orn, Dbu, Dpr or Abu; R$_6$ is β-D-NAL, (B)D-Trp, (A')D-Phe, (D)D-Har, D-Tyr, (C)D-His, D-PAL, (D)D-Arg, D-Leu, D-Ile, D-Val, D-Nle, D-Ala, D-Pro, D-Ser(OtBu), or D-Nva; A' is A, NH$_2$, NHCH$_3$ or gua; B is H, NO$_2$, NH$_2$, OCH$_3$, F, Cl, Br, CH$_3$, N$^{in}$For or N$^{in}$Ac; C is H, imBzl or dinitrophenol; D is H or di-lower alkyl; R$_7$ is Nle, Leu, NML, Phe, Met, Nva, Tyr, Trp or PAL; E is H, OH or dehydro and R$_{10}$ is Cys, Asp, Glu, Orn, Dbu, Dpr or Abu; provided however that when R$_4$ is Cys or Abu, R$_{10}$ is cys or Abu; when R$_4$ is Asp or Glu, R$_{10}$ is Orn, Dbu or Dpr; and when R$_4$ is Orn, Dbu or Dpr, R$_{10}$ is Asp or Glu and provided further that when R$_1$ is D-Cys or D-Abu, R$_3$ is D-Cys or D-Abu; when R$_1$ is D-Asp, D-Glu, D-Hgl or D-Hhg, R$_3$ is D-Lys, D-Hly, D-Hhl, D-Orn, D-Dbu or D-Dpr; and when R$_1$ is D-Lys, D-Hly, D-Hhl, D-Orn, D-Dbu or D-Dpr, R$_3$ is D-Asp, D-Glu, D-Hgl or D-Hhg.

It may be desirable to have a longer cyclizing linkage between the two residues in the 1- and 3-positions than the dicarba linkage between two D-Abu residues, and in such an instance, peptides may be synthesized having the formula:

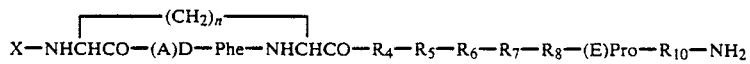

wherein X is hydrogen or an acyl group having 7 or less carbon atoms; A is H, Cl, F, NO$_2$, CH$_3$, OCH$_3$, C$^a$Me/4Cl, Cl$_2$ or Br; n=4 to 11; R$_4$ is Ser, Cys, Asp, Glu, Orn, Dbu, Dpr or Abu; R$_5$ is Tyr, Glu, Hgl or Hhg; R$_6$ is β-D-NAL, (B)D-Trp, (A')D-Phe, (D)D-Har, D-Tyr, (C)D-His, D-PAL, (D)D-Arg, D-Leu, D-Ile, D-Val, D-Nle, D-Ala, D-Pro, D-Ser(OtBu), or D-Nva; A' is A, NH$_2$, NHCH$_3$ or gua; B is H, NO$_2$, NH$_2$, OCH$_3$, F, Cl, Br, CH$_3$, N$^{in}$For or N$^{in}$Ac; C is H, imBzl or dinitrophenol; D is H or di-lower alkyl; R$_7$ is Nle, Leu, NML, Phe, Met, Nva, Tyr, Trp or PAL; E is H, OH or dehydro; R$_8$ is (D)Arg, (D)Har, Lys, Hly or Hhl and R$_{10}$ is Gly, D-Ala, Cys, Asp, Glu, Orn, Dbu, Dpr or Abu; provided however that when R$_4$ is Cys or Abu, it is bonded to R$_{10}$ which is Cys or Abu; when R$_4$ is Asp or Glu, it is bonded to R$_{10}$ which is Orn, Dbu or Dpr; when R$_4$ is Orn, Dbu or Dpr, it is bonded to R$_{10}$ which is Asp or Glu; and when R$_5$ is Glu, Hgl or Hhg, it is bonded to R$_8$ which is Lys, Hly or Hhl. When the residues in positions 1 and 3 are both Abu, n=4; however, preferably, n=7 to 9. Such peptide may be monocyclic, dicyclic or tricyclic.

The peptides of the present invention can be synthesized by classical solution synthesis or by a solid phase technique using a chloromethylated resin, a hydroxymethylated resin, a methylbenzhydrylamine resin (MBHA), a benzhydrylamine (BHA) resin or any other suitable resin known in the art. The solid phase synthesis is conducted in a manner to stepwise add the amino acids in the chain in the manner set forth in detail in the U.S. Pat. No. 4,211,693. Side-chain protecting groups, as are well known in the art, are preferably added to the residues to be employed in the synthesis having particularly labile side chains and may optionally be added to others, such as Trp, before these amino acids are coupled to the chain being built upon the resin. Such synthesis provides the fully protected intermediate peptidoresin.

Chemical intermediates made generally in accordance with the invention to produce the preferred bicyclic peptides may be represented by Formula II:

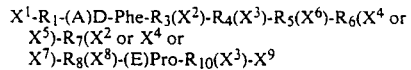

wherein: X$^1$ is an alpha-amino protecting group of the type known to be useful in the art in the stepwise synthesis of polypeptides and when X in the desired peptide composition is a particular acyl group, that group may be used as the protecting group. Among the classes of alpha-amino protecting groups covered by X$^1$ are (1) acyl-type protecting groups, such as formyl(For), trifluoroacetyl, phthalyl, p-toluenesulfonyl(Tos), benzoyl(Bz), benzenesulfonyl, o-nitrophenylsulfenyl(Nps), tritylsulfenyl, o-nitrophenoxyacetyl, acrylyl(Acr), chloroacetyl, acetyl(Ac) and γ-chlorobutyryl; (2) aromatic urethan-type protecting groups, e.g., benzyloxycarbonyl(Z), fluorenylmethyloxycarbonyl(Fmoc) and substituted benzyloxycarbonyl, such as p-chlorobenzyloxycarbonyl(ClZ), p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred alpha-amino protecting group is Boc, particularly when X is hydrogen.

$X^2$ is hydrogen or a suitable protecting group for the indole nitrogen of Trp, such as Bz.

$X^3$ is a protecting group for the sulfhydryl group of Cys, preferably p-methoxybenzyl(MeOBzl), p-methylbenzyl, acetamidomethyl, trityl or Bzl; or a suitable protecting group for an amino side chain, e.g. 2Cl-Z or t-amyloxycarbonyl; or a suitable, preferably hydrazine-labile, protecting group for a carboxyl side chain, such as OBzl(benzyl ester); or is a direct bond where the cyclic form results from a carba or dicarba bond.

$X^4$ is hydrogen or a protecting group for the phenolic hydroxyl group of Tyr selected from the group consisting of tetrahydropyranyl, tert-butyl, trityl, benzyl, Z, 2-bromobenzyloxycarbonyl (2BrZ) and 2,6-dichlorobenzyl(DCB). 2BrZ is preferred.

$X^5$ is a protecting group for a side chain guanidino group, such as that in Arg, or for the imidazole group of His, such as nitro, Tos, trityl, adamantyloxycarbonyl, Z and 2,4-dinitrophenyl(DNP), or $X^5$ may be hydrogen, which means there is no protection on the side chain group atoms. Tos is generally preferred.

$X^6$ is hydrogen or a base-labile protecting group for a side-chain carboxyl group, preferably fluorenylmethyl ester (OFm), or is a covalent bond.

$X^7$ is hydrogen or a protecting group for Met, such as oxygen.

$X^8$ is a base-labile protecting group for an amino side chain group, preferably Fmoc, or is a covalent bond.

$X^9$ may be O-CH$_2$-[resin support], -NH-[resin support], OH, ester or NH$_2$.

The criterion for selecting side-chain protecting groups for $X^2$-$X^8$ is that the protecting group should be stable to the reagent under the reaction conditions selected for removing the alpha-amino protecting group (preferably Boc) at each step of the synthesis. The protecting group should not be split off under coupling conditions but should be removable upon completion of the synthesis of the desired amino acid sequence under reaction conditions that will not alter the peptide chain. The protecting groups $X^6$ and $X^8$ in some syntheses should be removable without the removal of the protecting group $X^3$.

When the $X^9$ group is -O-CH$_2$-[resin support], the ester moiety of one of the many functional groups of a polystyrene resin support is being represented. When the $X^9$ group is -NH-[resin support], an amide bond connects $R_{10}$ to a BHA resin or to a MBHA resin.

When X is acetyl, for example, in the final formula, it may be possible to employ it as the $X^1$ protecting group for the alpha-amino group of D-NAL or whatever amino acid is used in the 1-position by adding it before the coupling of this last amino acid to the peptide chain. However, a reaction is preferably carried out with the peptide on the resin (after deblocking the alpha-amino group while the side-chain groups remain protected), e.g. by reacting with acetic acid in the presence of dicyclohexyl carbodiimide (DCC) or preferably with acetic anhydride or by another suitable reaction as known in the art.

In making the preferred bicyclic peptides, one cyclization is preferably effected of the 6-residue peptide intermediate while it is a part of the peptidoresin. After this cyclization is effected, the synthesis of the decapeptide is completed. If a tricyclic peptide is being synthesized or if an amido bond is being established between the 1- and 3-position residues, cyclization may be carried out on the resin between the 1- and 3-position residues. The protected peptide is then suitably cleaved from the resin, e.g., from a hydroxymethylated resin or a chloromethylated resin support by ammonolysis, as is well known in the art, to yield the fully protected amide intermediate, or alternatively, from a benzhydrylamine resin with hydrofluoric acid (HF) causing deprotection as well as cleavage of the peptide.

The final cyclizing steps for the GnRH peptide analog depend, of course, upon the type of linkage which is intended between the residues in the 4- and 10-positions; they should also take into consideration the amide bond linkage between the residues in positions 5 and 8 as well as any linkage which optionally may have been formed between the 1- and the 3-position residues. It is generally preferred to carry out the final cyclizing step to form the bond between the position 4- and 10-residues following the cleavage from the resin. Such a disulfide form of bond is obtained by oxidizing using a ferricyanide solution, preferably as described in Rivier et al., *Biopolymers*, Vol. 17 (1978), 1927–38, or by air oxidation, or in accordance with other known procedures.

When the cyclization is via an amide bond between a side-chain amino group of the 4-position residue and a side-chain carboxyl group of the 10-position residue (which may be preferred), or vice-versa, it is preferable to synthesize the protected peptide on an MBHA or BHA resin and to derivatize the benzyl ester of the carboxyl acid side chain to the hydrazide while the peptide is still attached to the resin. This can be accomplished by using OBzl as a protecting group for the carboxyl side-chain of the residue to be involved in the amide-bond bridge. Following this selective hydrazide activation, deprotection of the remainder of the side-chain protecting groups and cleavage from the resin are effected. Then reaction to accomplish cyclization is carried out by treating with isoamylnitrite and a strong acid, such as HCl, to generate the azide which in turn reacts with the free amino group on the side chain of the 10-position residue, after a neutralization step, generating the amide bond.

Analogs of GnRH including the equivalent of modified cysteine residues in the 4- and 10-positions wherein the disulfide linkage has been replaced by —CH$_2$— linkage are referred to as dicarba. If only one of the sulfhydryl groups is replaced by a CH$_2$-group, it is referred to as carba, e.g., [carba$^4$, Cys$^{10}$]-GnRH. In general, cyclizations of peptides in this overall fashion are exemplified by the teachings of the following U.S. Pat. Nos. 4,115,554, (Sept. 19, 1978); 4,133,805 (Jan. 9, 1979); 4,140,767 (Feb. 20, 1979); 4,161,521 (July 17, 1979); 4,191,754 (Mar. 4, 1980); 4,238,481 (Dec. 9, 1980); 4,244,947 (Jan. 13, 1981); and 4,261,885 (Apr. 14, 1981). Viewed from the aspect of the ultimate peptide, the location which would otherwise have been occupied by a Cys residue instead contains a residue of alpha-amino butyric acid(Abu). When preparing peptides having such a dicarba or carba-S linkage or a longer chain dicarba linkage, the procedure set forth in either U.S. Pat. No. 4,161,521 or U.S. Pat. No. 4,703,106 may be employed (the disclosures of which patents are incorporated herein by reference); in either case, in the intermediate of Formula II, $X^3$ is a direct bond to the other residue.

Thus, for example, the invention also provides a method for making certain preferred bicyclic peptide or a nontoxic salt thereof, which peptides have the Formula I:

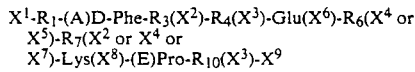

wherein X is hydrogen or an acyl group having ; or less carbon atoms; $R_1$ is dehydroPro, D-pGlu, (A)D-Phe, (B)D-Trp, Pro, or $\beta$-D-NAL; A is H,Cl, F, $NO_2$, $CH_3$, $OCH_3$, $C^aMe/4Cl$, $Cl_2$ or Br; B is H, $NO_2$, $NH_2$, $OCH_3$, F, Cl, Br, $CH_3$, $N^{in}For$ or $N^{in}Ac$; $R_3$ is D-PAL, $\beta$-D-NAL or (B)D-Trp; $R_4$ is Cys, Asp, Glu, Orn, Dbu, Dpr or Abu; $R_6$ is $\beta$-D-NAL, (B)D-Trp, (A')D-Phe, (D)D-Har, D-Tyr, (C)D-His, D-PAL, (D)D-Arg, D-Leu, D-Ile, D-Val, D-Nle, D-Ala, D-Pro, D-Ser(OtBu), or D-Nva; A' is A, $NH_2$, $NHCH_3$ or gua; C is H, imBzl or di nitrophenyl; D is H or di-lower alkyl; $R_7$ is Nle, Leu, NML, Phe, Met, Nva, Tyr, Trp or PAL; E is H, OH or dehydro and $R_{10}$ is Cys, Asp, Glu, Orn, Dbu, Dpr or Abu; provided however that when $R_4$ is Cys or Abu, $R_{10}$ is Cys or Abu; when $R_4$ is Asp or Glu, $R_{10}$ is Orn, Dbu or Dpr; and when $R_4$ is Orn, Dbu or Dpr, Re is Asp or Glu; which method comprises (a) forming an intermediate compound having the Formula II:

$X^1$-$R_1$-(A)D-Phe-$R_3(X^2)$-$R_4(X^3)$-Glu($X^6$)-$R_6(X^4$ or $X^5)$-$R_7(X^2$ or $X^4$ or $X^7)$-Lys($X^8$)-(E)Pro-$R_{10}(X^3)$-$X^9$ wherein $X^1$ is hydrogen or an alpha-amino protecting group; $X^2$ is hydrogen or a protecting group for an indole nitrogen; $X^3$ is a direct bond, hydrogen or a protecting group for Cys or for a side-chain amino or carboxyl group; $X^4$ is hydrogen or a protecting group for a phenolic hydroxyl group of Tyr; $X^5$ is either hydrogen or a protecting group for a guanidino or imidazole side chain; $X^6$ is a base-labile protecting group for a carboxyl side chain or a direct bond; $X^7$ is a protecting group for Met; $X^8$ is a base-labile protecting group for a side-chain amino or a direct bond; and $X^9$ is selected from the group consisting of O—$CH_2$—(resin support), —NH—(resin support), esters, and amides; (b) splitting off one or more of the groups $X^1$ to $X^8$ and/or cleaving from any resin support included in $X^9$; (c) optionally creating a cyclizing bond between $R_4$ and $R_{10}$ if not already present and, if desired, (d) converting a resulting peptide into a nontoxic salt thereof. Preferably the intermediate for certain preferred bicyclic peptides has the Formula (III):

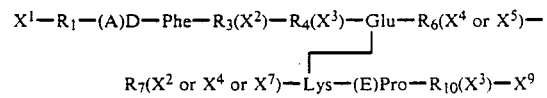

wherein $X^6$ and $X^8$ in Formula (II) constitute a direct amide bond. Preferably the intermediate for certain preferred tricyclic peptide has the Formula (IIIA):

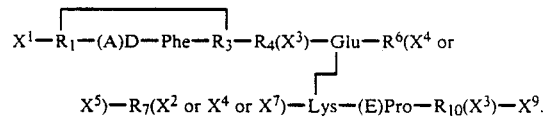

Purification of the peptide may be effected by ion exchange chromotography on a CMC column, followed by partition chromotography using the elution system: n-butanol;0.1N acetic acid (1:1 volume ratio) on a column packed with Sephadex G-25; however, it is preferably carried out by using HPLC, as known in the art and set forth specifically in J. Rivier, et al. *J. Chromatography*, 288 (1984) 303-328.

The peptides of the invention are effective at levels of less than 100 micrograms per kilogram of body weight, when administered at about noon on the day of proestrous, to prevent ovulation in female rats. For prolonged suppression of ovulation, it may be necessary to use dosage levels in the range of from about 0.1 to about 2.5 milligrams per kilogram of body weight. These antagonists are also effective to arrest spermatogenesis when administered to male mammals on a regular basis and can thus be used as contraceptives. Since these compounds will reduce testosterone levels (an undesired consequence in the normal, sexually active male), it may be reasonable to administer replacement dosages of testosterone along with the GnRH antagonist. These antagonists can also be used to regulate the production of gonadotropins and sex steroids for other purposes as indicated hereinbefore.

EXAMPLE I

Bicyclic peptides as indicated in TABLE I having the formula:

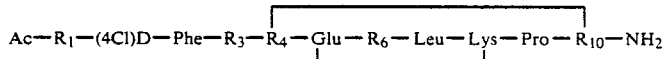

are prepared by the solid-phase procedure referred to above.

TABLE I

| | $R_1$ | $R_3$ | $R_4$ | $R_6$ | $R_{10}$ |
|---|---|---|---|---|---|
| 1 | $\beta$-D—2NAL | D—Trp | Asp | D—Arg | Dpr |
| 2 | " | " | Dpr | " | Asp |
| 3 | " | D—3PAL | Asp | $\beta$-D—2NAL | Dpr |
| 4 | dehydroPro | D—Trp | Cys | " | Cys |
| 5 | $\beta$-D—2NAL | " | " | " | " |
| 6 | " | D—3PAL | Dpr | D—3PAL | Asp |
| 7 | " | " | Orn | " | Asp |
| 8 | dehydroPro | $\beta$-D2NAL | Asp | $\beta$-D—2NAL | Dpr |

TABLE I-continued

|    | R₁       | R₃     | R₄  | R₆         | R₁₀ |
|----|----------|--------|-----|------------|-----|
| 9  | "        | D—3PAL | "   | D—Tyr      | Dpr |
| 10 | B-D—2NAL | D—Trp  | Glu | D—2PAL     | Dpr |
| 11 | "        | "      | Dbu | (4gua)D—Phe | Asp |
| 12 | "        | "      | "   | "          | "   |
| 13 | dehydroPro | "    | "   | D—Ala      | Glu |
| 14 | D—Trp    | D—4PAL | "   | D—Phe      | "   |
| 15 | D—pGlu   | D—Trp  | Dpr | D—Ile      | "   |
| 16 | D—Phe    | D—2PAL | "   | D—Val      | Asp |

For purposes of an example, a representative solid phase synthesis of Peptide No. 1 above, which is referred to as (Cyclo 4-10, 5-8) [Ac-β-D-2NAL¹, (4Cl)D-Phe², D-Trp³, Asp⁴, Glu⁵, D-Arg⁶, Lys⁸, Dpr¹⁰]-GnRH is set forth hereinafter. This peptide has the following formula:

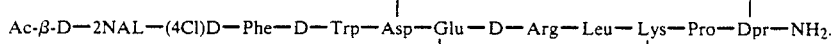

Ac-β-D—2NAL—(4Cl)D—Phe—D—Trp—Asp—Glu—D—Arg—Leu—Lys—Pro—Dpr—NH₂.

The other peptides are similarly synthesized and purified.

Five grams of a BHA resin are used, and Boc-protected Dpr is coupled to the resin over a 2-hour period in CH₂Cl₂ using a 3-fold excess of Boc derivative and DCC as an activating reagent. The Dpr residue attaches to the BHA residue by an amide bond.

Following the coupling of each amino acid residue, washing, deblocking and coupling of the next amino acid residue is carried out in accordance with the following schedule, using an automated machine, when beginning with about 5 grams of resin:

| STEP | REAGENTS AND OPERATIONS | MIX TIMES MIN. |
|------|-------------------------|----------------|
| 1 | CH₂Cl₂ wash-80 ml. (2 times) | 3 |
| 2 | Methanol(MeOH) wash-30 ml. (2 times) | 3 |
| 3 | CH₂Cl₂ wash-80 ml. (3 times) | 3 |
| 4 | 50 percent TFA plus 5 percent 1,2-ethanedithiol in CH₂Cl₂-70 ml. (2 times) | 10 |
| 5 | Isopropyl alcohol + 1% ethanedithiol wash-80 ml. (2 times) | 3 |
| 6 | TEA 12.5 percent in CH₂Cl₂-70 ml. (2 times) | 5 |
| 7 | MeOH wash-40 ml. (2 times) | 2 |
| 8 | CH₂Cl₂ wash-80 ml. (3 times) | 3 |
| 9 | Boc-amino acid (10 mmoles) in 30 ml. of either DMF or CH₂Cl₂, depending upon the solubility of the particular protected amino acid, (1 time) plus DCC (10 mmoles) in CH₂Cl₂ | 30–300 |
| 10 | MeOH wash-40 ml. (2 times) | 3 |
| 11 | TEA 12.5 percent in CH₂Cl₂-70 ml. (1 time) | 3 |
| 12 | MeOH wash-30 ml. (2 times) | 3 |
| 13 | CH₂Cl₂ wash-80 ml. (2 times) | 3 |

Should the synthesis be manually performed, after step 13, an aliquot may be taken for a ninhydrin test. If the test is negative, proceed to step 1 for coupling of the next amino acid; if the test is positive or slightly positive, go back and repeat steps 9 through 13.

The above schedule is used for coupling of each of the amino acids of the peptide of the invention after the first amino acid has been attached. NᵅBoc protection is used for each of the remaining amino acids throughout the synthesis. NᵅBoc-β-D-2NAL is prepared by a method known in the art, e.g. as described in detail in U.S. Pat. No. 4,234,571, issued Nov. 18, 1980. The side chain of D-Arg is protected with Tos. Fmoc is used as a side-chain protecting group for the amino group of Lys; whereas Z is used to protect the side-chain amino group of Dpr. The carboxyl side chain of Glu is protected with OFm, whereas the carboxyl side chain of Asp is protected with OBzl. NᵅBoc-β-D-2NAL is introduced as the final amino acid. Boc-D-Arg(Tos), which has low solubility in CH₂Cl₂, is coupled using a DMF:CH₂Cl₂ mixture.

Following the assembly of a hexapeptide intermediate on a MBHA resin having the formula: Boc-Glu(OFm)-D-Arg(Tos)-Leu-Lys(Fmoc)-Pro-Dpr(Z)-MBHA resin support. The deprotection of the Glu and Lys residues and initial cyclization are carried out by treatment with 50 ml of 20 volume % piperidine in DMF for 1 hour at about 22° C., followed by washing. Then the peptidoresin, about 5 meq. (2.2 gm) of BOP [Benzotriazolyl-N-oxytris(dimethylamino)-phosphonium hexafluorophosphate] and 15 meq. of diisopropylethylamine are suspended and stirred for 2 hours at room temperature to effect cyclization between the side chains of Glu and Lys. The peptidoresin is filtered and then washed with DMF, MeOH, CH₂Cl₂ and MeOH. Thereafter, the Boc-protecting group is removed from the cyclic hexapeptide, and the synthesis of the decapeptide is completed to produce the intermediate:

Boc-β-D—2NAL—(4Cl)D—Phe—D—Trp—Asp(OBzl)—

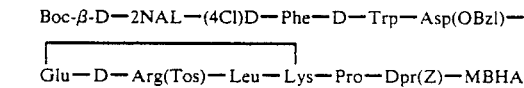

Glu—D—Arg(Tos)—Leu—Lys—Pro—Dpr(Z)—MBHA resin support.

After deblocking the alpha-amino group at the N-terminus using trifluoroacetic acid(TFA), acetylation is achieved using a large excess of acetic anhydride in dichloromethane. Thereafter, about 4 g. of protected-peptidyl resin is suspended at room temperature in 40 ml of DMF, and 1 ml. of anhydrous hydrazine (30–40× excess) is added to it under continuous stirring. Nitrogen is bubbled through the reactive mixture, and continuous stirring is effected in a closed vial for 48 hours. The resin is filtered, washed with DMF, MeOH, CH₂Cl₂ and MeOH, and finally dried.

About 4 g. of the protected peptide-hydrazide-resin is treated with 10–15 ml of distilled HF, in the presence of 1.5 ml of anisole as a scavenger, at 0° C. for 60 minutes to remove the remaining protecting groups and cleave the peptide from the resin. HF is removed under high vacuum, and the peptide is precipitated with anhydrous ethyl ether. The solid is collected, dissolved in 50 ml CH₃CN:H₂O (1:1) and lyophilized. It is then purified using RP-HPLC prior to final cyclizing.

1000 mg of the peptide-hydrazide is dissolved in 15 ml of DMF, cooled to −25° C., and N₂ gas is bubbled therethrough. 0.56 ml (about 2.25 mmol) of 4N HCl in dioxane is added, and finally 105 μl (about 0.78 mmol) of isoamylnitrite is added over ten minutes. Stirring at −25° C. is continued for 3 hours. The azide-solution is diluted with 1000 ml of precooled DMF (−25° C.); N,N diisopropylethylamine is added in suitable portions to give a final pH of 7.8. The pH is checked and readjusted several times.

The solution is stored at 4° C. for 3 days, then evaporated to dryness in high vacuum. The residue is triturated in the presence of ethyl ether. The solid is collected and dried in vacuum.

Final purification of the peptide is then effected by two RP-HPLC separations. The first preferably uses a TEAP (triethylammonium phosphate) buffer system, and the second uses a TFA buffer system, as described in detail in the *J. Chromatography* article.

The peptide is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain. The optical rotation of Peptide No. 1 is measured on a photoelectric polarimeter as $[\alpha]_D^{22} = -49.5° \pm 1 (c=1, 50\%$ acetic acid).

When a peptide, such as No. 4, has a second cyclizing bond in the form of a disulfide bond between the side chains of the residues in the 4- and 10-positions, this bond may be made by air-oxidation of the cyclic decapeptide after its removal from the resin. As an example of a suitable procedure, the intermediate is prepared having the formula:

duce the amount of LH released by 3 nanomolar GnRH is compared to that of the present standard peptide.

In vivo testing determines effectiveness to prevent ovulation in female rats. In this test, a specified number of mature female Sprague-Dawley rats, e.g. five to ten, each having a body weight from 225 to 250 grams, is injected with a specified microgram dosage of peptide in either saline or bacteriostatic water at about noon on the day of proestrous. Proestrous is the afternoon of ovulation. A separate female rat group is used as a control to which the peptide is not administered. Each of the control female rats ovulates on the evening of proestrous; of the rats treated, the number of them which ovulate is recorded. Peptide No. 1 is considered to be significantly effective to prevent ovulation of female rats at a very low dosage; it is considered to be totally effective at a dose of about 500 micrograms Kg of body weight and may be effective at about 100 µg/Kg.

All peptides listed in Table I are considered effective to block GnRH-induced LH secretion in vitro at a reasonable concentration, and all are considered to be effective to prevent ovulation of female mammals at reasonable dosages.

EXAMPLE II

Peptides as indicated in TABLE II having the formula:

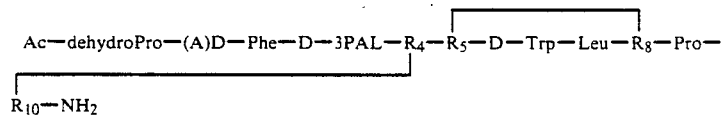

are prepared by the solid-phase procedure referred to above.

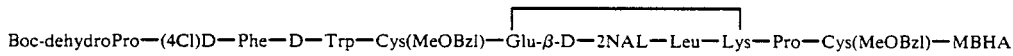

resin support.

After alpha-amino deprotection and acetylation as described above, cleavage of the peptide from the resin and deprotection of the Cys side chains is very readily effected at 0° C. with HF, with anisole added as a scavenger prior to HF treatment. After the removal of HF under vacuum, the resin is extracted with 50% acetic acid, and the washed peptide is then air-oxidized for about 24 hours at about 22° C. to create a disulfide linkage between the Cys residues in each molecule. Finally, lyophilization is carried out to provide a crude peptide powder.

The peptides are assayed in vivo and are also tested in vitro using dissociated rat pituitary cells maintained in culture for 4 days prior to the assay. The levels of LH mediated in response to the application of peptides is assayed by specific radioimmunoassay for rat LH. Control dishes of cells only receive a measure which is 3 nanomolar in GnRH; experimental dishes receive a measure 3 nanomolar in GnRH plus a measure having either the present standard antagonist for comparison purposes i.e. [Ac-dehydroPro[1], (4F)D-Phe[2], D-Trp[3,6]]-GnRH or the test peptide, in concentrations ranging from 0.01 to 10 nanomolar. The amount of LH secreted in the samples treated only with GnRH is compared with that secreted by the samples treated with the peptide plus GnRH. The ability of the test peptide to re-

TABLE II

| | A | $R_4$ | $R_5$ | $R_8$ | $R_{10}$ |
|---|---|---|---|---|---|
| 17 | 4F | Cys | Glu | Lys | Cys |
| 18 | " | Dpr | " | Hly | Asp |
| 19 | 4Cl | Orn | " | Hhl | " |
| 20 | " | Dbu | Hgl | Lys | Glu |
| 21 | " | " | " | Hly | Asp |
| 22 | " | Dpr | " | Hhl | " |
| 23 | 4Br | " | Hhg | " | Glu |
| 24 | " | Dbu | " | Lys | " |
| 25 | H | " | " | Hly | Asp |
| 26 | 4NO$_2$ | " | Glu | " | " |
| 27 | " | Asp | " | Hhl | Dpr |
| 28 | 2,4Cl$_2$ | " | " | " | Dbu |
| 29 | " | Glu | Hgl | " | " |
| 30 | C$^\alpha$Me/4Cl | Abu | " | Lys | Cys |
| 31 | 3,4Cl$_2$ | Cys | " | Hhl | Abu |

In vitro and/or in vivo testing of the peptides specified in Table II shows that the peptides listed in Table II are considered effective to block GnRH-induced LH secretion in vitro at a reasonable concentration. All of the peptides are considered to be effective to prevent ovulation of female mammals at low dosages.

EXAMPLE III

Peptides as indicated in TABLE III having the formula:

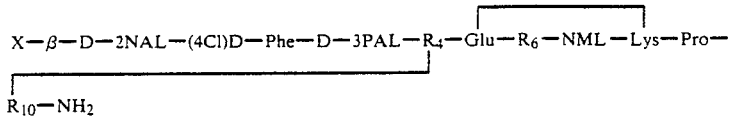

are prepared by the solid-phase procedure referred to above.

TABLE III

|    | X   | $R_4$ | $R_6$         | $R_{10}$ |
|----|-----|-------|---------------|----------|
| 32 | Ac  | Cys   | D—Arg         | Abu      |
| 33 | Acr | Abu   | D—Tyr         | Abu      |
| 34 | For | Asp   | "             | Dpr      |
| 35 | Bz  | "     | D—Arg         | Dbu      |
| 36 | Ac  | Dpr   | D—His         | Asp      |
| 37 | Vac | "     | $(Et_2)$D—Har | Glu      |
| 38 | Acr | Orn   | (4gua)D—Phe   | "        |
| 39 | Ac  | Dbu   | D—3PAL        | Asp      |
| 40 | Acr | Cys   | D—His         | Cys      |
| 41 | Ac  | Orn   | $(Et_2)$D—Arg | Asp      |
| 42 | "   | Dpr   | D—2PAL        | "        |
| 43 | Vac | "     | $(4NH_2)$D—Phe | Glu     |
| 44 | Bz  | Glu   | D—Har         | Dpr      |

Peptides such as Nos. 32 and 33 are synthesized by employing the general teaching of U.S. Pat. No. 4,161,521.

In vitro and/or in vivo testing of the peptides specified in Table III shows that the peptides listed in Table III are considered effective to block GnRH-induced LH secretion in vitro at a reasonable concentration. All of the peptides are considered to be effective to prevent ovulation of female mammals at low dosages.

EXAMPLE IV

Peptides as indicated in TABLE IV having the formula:

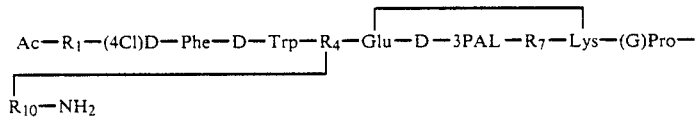

are prepared by the solid-phase procedure referred to above.

TABLE IV

|    | $R_1$        | $R_4$ | $R_7$   | G       | $R_{10}$ |
|----|--------------|-------|---------|---------|----------|
| 45 | β-D—2NAL     | Asp   | Nle     | H       | Dpr      |
| 46 | (1Ac)D—Trp   | "     | Met     | OH      | "        |
| 47 | (6Br)D—Trp   | "     | Tyr     | H       | Dbu      |
| 48 | (5F)D—Trp    | "     | Nle     | dehydro | "        |
| 49 | $(6NO_2)$D—Trp | "   | Met     | "       | Dbu      |
| 50 | (5Cl)D—Trp   | "     | Tyr     | H       | Dpr      |
| 51 | (4Cl)D—Phe   | "     | Phe     | "       | Orn      |
| 52 | (4F)D—Phe    | "     | 4F—D—Phe | "      | "        |
| 53 | $(2,4Cl_2)$D—Phe | Glu | NML  | OH      | "        |
| 54 | dehydroPro   | "     | Nle     | "       | Dbu      |
| 55 | β-D—2NAL     | "     | Trp     | H       | "        |
| 56 | $(6OCH_3)$D—Trp | "  | Leu     | "       | Dpr      |
| 57 | $(5NH_2)$D—Trp | "   | Nva     | "       | "        |
| 58 | $(4NO_2)$D—Phe | "   | NML     | "       | "        |
| 59 | dehydroPro   | "     | Tyr     | OH      | "        |

All peptides listed in Table IV are considered effective to block GnRH-induced LH secretion in vitro at some reasonable concentration.

All of the peptides are considered to be effective to prevent ovulation of female mammals at low dosages.

EXAMPLE V

Peptides as indicated in TABLE V having the formula:

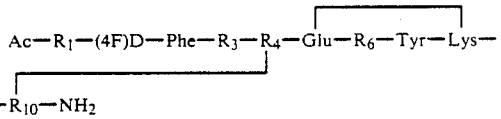

are prepared by the solid-phase procedure referred to above.

TABLE V

|    | $R_1$          | $R_3$            | $R_4$ | $R_6$            | $R_{10}$ |
|----|----------------|------------------|-------|------------------|----------|
| 60 | β-D—2NAL       | $(6NO_2)$D—Trp   | Cys   | D—Arg            | Cys      |
| 61 | "              | $(5CH_3)$D—Trp   | "     | (DNP)D—His       | Abu      |
| 62 | "              | $(5OCH_3)$D—Trp  | "     | (4gua)D—Phe      | Cys      |
| 63 | dehydroPro     | β-D—2NAL         | "     | $(6NO_2)$D—Trp   | "        |
| 64 | "              | β-D—1NAL         | "     | D—Val            | Abu      |
| 65 | β-D—2NAL       | (1For)D—Trp      | "     | $(Et_2)$D—Arg    | "        |
| 66 | "              | (5F)D—Trp        | Abu   | $(5NH_2)$D—Trp   | Cys      |
| 67 | dehydroPro     | (5Cl)D—Trp       | "     | D—Tyr            | Abu      |
| 68 | "              | D—2PAL           | Glu   | D—Nle            | Dbu      |
| 69 | "              | (1Ac)D—Trp       | "     | (4F)D—Phe        | Orn      |
| 70 | Pro            | D—3PAL           | Asp   | β-D—1NAL         | Dbu      |
| 71 | (1For)D—Trp    | "                | "     | $(4NHCH_3)$D—Phe | Dpr      |
| 72 | β-D—2NAL       | "                | Cys   | $(Ipr_2)$D—Arg   | Cys      |
| 73 | "              | $(5NH_2)$D—Trp   | "     | $(4NH_2)$D—Phe   | Abu      |
| 74 | β-D—1NAL       | (6Br)D—Trp       | "     | (1For)D—Trp      | Cys      |
| 75 | $(6CH_3)$D—Trp | D—4PAL           | Asp   | D—4PAL           | Dbu      |

In vitro and/or in vivo testing of the peptides specified in Table V shows that the peptides listed in Table V are considered effective to block GnRH-induced LH secretion in vitro at a reasonable concentration. All of the peptides are considered to be effective to prevent ovulation of female mammals at low dosages.

EXAMPLE VI

Peptides as indicated in TABLE VI having the formula:

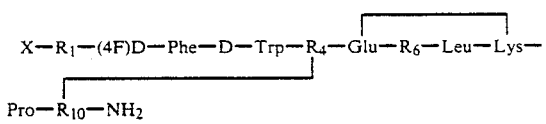

are prepared by the solid-phase procedure referred to above.

TABLE VI

| | X | $R_1$ | $R_4$ | $R_6$ | $R_{10}$ |
|---|---|---|---|---|---|
| 76 | Acr | dehydroPro | Asp | D—Val | Dpr |
| 77 | Ac | " | Dpr | β-D—2NAL | Asp |
| 78 | Ac | β-D—2NAL | Cys | (MeEt)D—Arg | Cys |
| 79 | Acr | Pro | Glu | D—Ser(OtBu) | Orn |
| 80 | H | dehydroPro | Dpr | (imBzl)D—His | Asp |
| 81 | Bz | (4Br)D—Pre | " | (5Cl)D—Trp | Glu |
| 82 | " | D—pGlu | " | (6Br)D—Trp | " |
| 83 | For | β-D—1NAL | " | D—Nva | Asp |
| 84 | " | dehydroPro | Cys | (Ipr2)D—Har | Abu |
| 85 | Vac | β-D—2NAL | " | D—Pro | Cys |
| 86 | " | D—Phe | Dbu | D—Ile | Asp |
| 87 | H | dehydroPro | " | D—Ala | Glu |

In vitro and/or in vivo testing of the peptides specified in Table VI shows that the peptides listed in Table VI are considered effective to block GnRH-induced LH secretion in vitro at a reasonable concentration. All of the peptides are considered to be effective to prevent ovulation of female mammals at low dosages.

EXAMPLE VII

Peptides as indicated in TABLE VII having the formula:

$$Ac—R_1—(4Cl)D—Phe—R_3—R_4—Glu—R_6—Leu—Lys—Pro—R_{10}—NH_2$$

are prepared by the solid-phase procedure referred to above.

TABLE VII

| | $R_1$ | $R_3$ | $R_4$ | $R_6$ | $R_{10}$ |
|---|---|---|---|---|---|
| 88 | dehydroPro | (6NO2)D—Trp | Asp | β-D—2NAL | Dpr |
| 89 | " | " | " | D—Val | " |
| 90 | " | (6F)D—Trp | " | (4gua)D—Phe | " |
| 91 | " | " | " | D—Nva | " |
| 92 | " | (5OCH3)D—Trp | " | D—Pro | " |
| 93 | " | " | " | D—2PAL | " |
| 94 | β-D—2NAL | (1Ac)D—Trp | Glu | (Me2)D—Har | " |
| 95 | " | (1For)D—Trp | " | (5CH3)D—Trp | Dbu |
| 96 | dehydroPro | (6Br)D—Trp | Abu | D—Nle | Cys |
| 97 | " | " | " | D—Leu | Abu |
| 98 | " | (6CH3)D—Trp | " | β-D—2NAL | Cys |
| 99 | " | (6NH2)D—Trp | Asp | (4NH2)D—Phe | Dpr |
| 100 | " | (5NH2)D—Trp | " | D—Ala | " |

In vitro and/or in vivo testing of the peptides specified in Table VII shows that the peptides listed in Table VII are considered effective to block GnRH-induced LH secretion in vitro at a reasonable concentration. All of the peptides are considered to be effective to prevent ovulation of female mammals at low dosages.

EXAMPLE VII

Peptides as indicated in TABLE VIII having the formula:

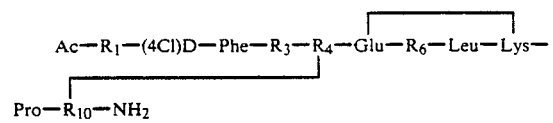

are prepared by the solid phase procedure referred to above.

TABLE VIII

| | $R_1$ | $R_4$ | $R_6$ | $R_7$ | $R_{10}$ |
|---|---|---|---|---|---|
| 101 | β-D—2NAL | Cys | (5NO2)D—Trp | Leu | Cys |
| 102 | " | " | D—3PAL | " | Abu |
| 103 | " | Abu | β-D—2NAL | " | Cys |
| 104 | " | " | (EtBu)D—Arg | " | Abu |
| 105 | dehydroPro | " | β-D—2NAL | 3PAL | Cys |
| 106 | " | Dpr | (4NO2)D—Phe | Tyr | Glu |
| 107 | β-D—2NAL | Dbu | D—3PAL | NML | " |
| 108 | " | Dpr | β-D—1NAL | 4PAL | Glu |
| 109 | " | Orn | (imBzl)D—His | Leu | " |
| 110 | " | Asp | (6NO2)D—Trp | " | Dpr |
| 111 | " | Glu | D—Tyr | " | " |
| 112 | " | " | (1For)D—Trp | Phe | Dbu |
| 113 | " | " | (6F)D—Trp | NML | " |
| 114 | (CᵃMe/4Cl)D—Phe | " | (4Cl)D—Phe | Nle | Orn |
| 115 | Pro | Asp | (imBzl)D—His | Met | " |
| 116 | dehydroPro | " | (6OCH3)D—Trp | Nva | Dbu |
| 117 | " | " | (5CH3)D—Trp | " | Dpr |
| 118 | " | " | (1Ac)D—Trp | (4F)Phe | " |
| 119 | " | " | D—Nle | NML | Dbu |
| 120 | " | Cys | D—Arg | Nle | Abu |
| 121 | " | " | β-D—2NAL | Trp | Cys |
| 122 | Pro | Dpr | (2,4Cl2)D—Phe | Nva | Asp |
| 123 | β-D—2NAL | " | β-D—1NAL | Tyr | " |
| 124 | " | Dbu | (5Cl)D—Trp | Met | " |
| 125 | (4Cl)D—Phe | " | (4Br)D—Phe | 3PAL | "(acetate salt) |

The peptides described in TABLE VIII are tested in vivo to determine their effectiveness to prevent ovulation in female rats. All of them are considered to prevent ovulation of female rats at a low dosage, and to be totally effective at a dose of about 500 micrograms.

EXAMPLE IX

Peptides as indicated in TABLE IX having the formula:

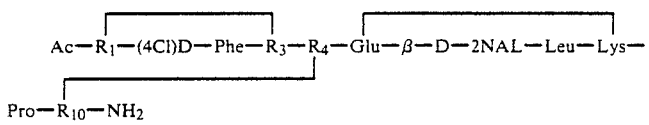

are prepared by the solid-phase procedure referred to above.

TABLE IX

| | $R_1$ | $R_3$ | $R_4$ | $R_{10}$ |
|---|---|---|---|---|
| 126 | D—Glu | D—Lys | Glu | Dbu |
| 127 | D—Dbu | D—Hgl | " | Orn |
| 128 | D—Cys | D—Abu | Asp | Dbu |
| 129 | D—Asp | D—Orn | " | Dpr |
| 130 | " | D—Hly | Cys | Cys |
| 131 | D—Glu | D—Lys | " | Abu |
| 132 | D—Hhg | D—Hhl | Orn | Asp |
| 133 | D—Cys | D—Cys | Asp | Dbu |
| 134 | D—Dpr | D—Asp | Cys | Cys |
| 135 | D—Hly | D—Glu | " | Abu |
| 136 | D—Orn | D—Asp | Orn | Asp |
| 137 | D—Hhl | D—Hhg | " | " |
| 138 | D—Abu | D—Abu | Asp | Dpr |
| 139 | D—Abu | D—Cys | " | " |
| 140 | D—Hgl | D—Orn | Abu | Cys |

The tricyclic peptides are made as generally explained hereinbefore through the steps of synthesizing the peptidoresin containing the cyclic hexapeptide, as set forth in Example I. Then the appropriate last 4 residues are added. For example, with respect to Peptide No. 126, after the Boc-protecting group is removed from the cyclic hexapeptide, the synthesis of the decapeptide is completed to produce the intermediate: Boc-D-Glu(OFm)-(4Cl)D-Phe-D-Lys(Fmoc)-Glu(OBzl)-Glu-$\beta$-D-2NAL-Leu-Lys-Pro-Dbu( Z)-MBHA resin support.

Following the assembly of the complete decapeptide intermediate on the MBHA resin, deprotection and cyclization of the D-Glue and D-Lys residues is carried out by treatment in the same manner as the deprotection and cyclization of Glu and Lys residues, i.e., treatment with piperidine, followed by washing, followed by treatment with BOP and diisopropylethylamine to effect cyclization between the side chains of D-Glu and D-Lys. The peptidoresin is filtered, washed with DMF, MeOH, CH$_2$Cl$_2$ and MeOH.

After deblocking the alpha-amino group at the N-terminus using trifluoroacetic acid(TFA), acetylation is achieved using a large excess of acetic anhydride in dichloromethane. Thereafter, the protected-peptidyl resin is suspended at room temperature in DMF, and anhydrous hydrazine is added to it under continuous stirring while nitrogen is bubbled therethrough. After 48 hours, the resin is filtered, washed with DMF, MeOH, CH$_2$Cl$_2$ and MeOH, dried and treated with distilled HF, in the presence of anisole as a scavenger, to remove the remaining protecting groups and cleave the peptide from the resin. After removal of HF, the peptide is precipitated with anhydrous ethyl ether, collected, and lyophilized. It is then purified using RP-HPLC, as in Example I, prior to final cyclizing, which is effected as set forth in Example I to achieve the third amide bond. Final purification of the tricyclic peptide is then effected as set forth in Example I.

In making a peptide, such as No. 133, the disulfide bond between the D-Cys residues in the 1- and 3-positions is preferably effected by oxidation prior to conversion of the linear peptide to the azide.

In vitro and/or in vivo testing of the peptides specified in Table IX shows that the peptides listed in Table IX are considered effective to block GnRH-induced LH secretion in vitro at a reasonable concentration. All of the peptides are considered to be effective to prevent ovulation of female mammals at low dosages.

EXAMPLE X

Bicyclic peptides as indicated in TABLE X having the formula:

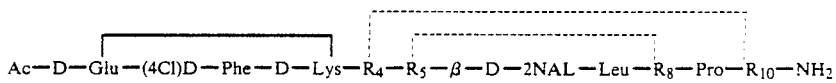

with a second cyclizing bond between either $R_5$ and $R_8$ or $R_4$ and $R_{10}$ are prepared by the solid-phase procedure referred to above.

TABLE X

| | $R_5$ | $R_8$ | $R_4$ | $R_{10}$ |
|---|---|---|---|---|
| 141 | Glu | Lys | Ser | D—Ala |
| 142 | " | Hly | " | Gly |
| 143 | Hgl | " | Orn | " |
| 144 | " | Hhl | Dbu | D—Ala |
| 145 | Hhg | " | Dpr | " |
| 146 | Tyr | Har | " | Dbu |
| 147 | " | (Et$_2$)Har | Abu | Cys |
| 148 | " | Arg | Asp | Dbu |
| 149 | " | (Ipr$_2$)Har | Glu | Dpr |
| 150 | " | (Et$_2$)Arg | Cys | Cys |
| 151 | " | (Ipr$_2$)Arg | Abu | Abu |
| 152 | " | Arg | Orn | Asp |

In vitro and/or in vivo testing of the peptides specified in Table X shows that the peptides listed in Table X are considered effective to block GnRH-induced LH secretion in vitro at a reasonable concentration. All of the peptides are considered to be effective to prevent ovulation of female mammals at low dosages.

EXAMPLE XI

Monocyclic peptides as indicated in TABLE XI having the formula:

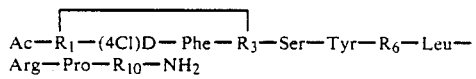

are prepared by the solid-phase procedure referred to above.

TABLE XI

| | R₁ | R₃ | R₆ | R₁₀ |
|---|---|---|---|---|
| 153 | D—Asp | D—Lys | β-D—2NAL | D—Ala |
| 154 | D—Glu | " | " | " |
| 155 | D—Orn | D—Glu | " | Gly |
| 156 | D—Glu | D—Orn | " | D—Ala |
| 157 | Orn | Asp | D—3PAL | " |
| 158 | Asp | Dpr | D—Arg | " |
| 159 | " | Lys | β-D—2NAL | " |
| 160 | Glu | D—Lys | " | " |
| 161 | D—Abu | D—Abu | D—3PAL | Gly |
| 162 | D—Lys | Glu | " | " |
| 163 | D—Asp | Dbu | D—Leu | D—Ala |
| 164 | D—Glu | D—Hly | D—3PAL | D—Ala |
| 165 | D—Lys | D—Hgl | " | Gly |
| 166 | D—Glu | D—Hhl | D—Arg | D—Ala |
| 167 | Lys | Hgl | D—3PAL | " |
| 168 | Hly | " | D—Arg | " |
| 169 | Hhg | Hly | β-D—2NAL | " |
| 170 | " | Hhl | " | " |

In vitro and/or in vivo testing of the peptides specified in Table XI shows that the peptides listed in Table X are considered effective to block GnRH-induced LH secretion in vitro at a reasonable concentration. All of the peptides are considered to be effective to prevent ovulation of female mammals at low dosages.

EXAMPLE XII

Monocyclic, bicyclic and tricyclic peptides as indicated in TABLE XII having the formula:

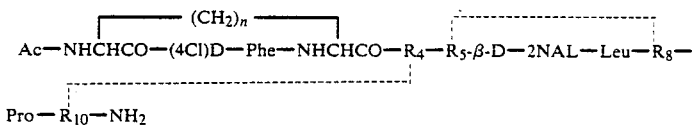

with the 1- and 3-position residues being in the D-isomer form, with a second cyclizing bond between either R₅ and R₈ or R₄ and R₁₀ being present in Peptides 175-179 and with second and third cyclizing bonds being present in Peptides 180-183 prepared by the solid-phase procedure referred to above.

TABLE XII

| | n | R₄ | R₅ | R₈ | R₁₀ |
|---|---|---|---|---|---|
| 171 | 7 | Ser | Tyr | Arg | D—Ala |
| 172 | 5 | " | " | (Ipr₂)Har | Gly |
| 173 | 8 | Orn | " | (Et₂)Arg | " |
| 174 | 6 | Dbu | " | Arg | D—Ala |
| 175 | 10 | Ser | Glu | Lys | " |
| 176 | 9 | " | Hgl | Hly | Gly |
| 177 | 7 | Abu | Tyr | (Et₂)Har | Cys |
| 178 | 11 | Asp | " | Arg | Dbu |
| 179 | 9 | Glu | " | Har | Dpr |
| 180 | 8 | Cys | Glu | Lys | Cys |
| 181 | 7 | Abu | " | Hly | Abu |
| 182 | 11 | Orn | Hgl | " | Asp |
| 183 | 10 | Glu | Hhg | Hhl | Dbu |

In vitro and/or in vivo testing of the peptides specified in Table XII shows that the peptides listed in Table XII are considered effective to block GnRH-induced LH secretion in vitro at a reasonable concentration. All of the peptides are considered to be effective to prevent ovulation of female mammals at low dosages.

The peptides of the invention are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like. For example, an aqueous solution of the peptide can be repeatedly treated with IN acetic acid and then lyophilized to yield the acetic acid salt thereof. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 10 micrograms to about 2.5 milligrams of the peptide per kilogram of the body weight of the host when given intravenously; although oral dosages will be higher, it is anticipated that the cyclic nature of these compounds will permit more effective oral administration. Overall, treatment of subjects with these peptides is generally carried out in the same manner as the clinical treatment using other antagonists of GnRH using a suitable carrier in which the peptide is soluble.

It may also be desirable to deliver the GnRH analog over prolonged periods of time, for example, for periods of one week to one year from a single administration, and slow release, depot or implant dosage forms may be utilized. For example, a dosage form may contain a pharmaceutically acceptable non-toxic salt of the compound which has a low degree of solubility in body fluids, for example, an acid addition salt with a polybasic acid; a salt with a polyvalent metal cation; or combination of the two salts. A relatively insoluble salt may also be formulated in a gel, for example, an aluminum stearate gel. A suitable, slow-release depot formulation for injection may also contain the GnRH analog or a salt thereof dispersed or encapsulated in a slow degrading, non-toxic or non-antigenic polymer such as a polylactic acid/polyglycolic acid polymer, for example, as described in U.S. Pat. No. 3,773,919. These compounds may also be formulated into silastic implants.

These peptides can be administered to mammals intravenously, subcutaneously, intramuscularly, orally, percutaneously, e.g. intranasally or intravaginally to achieve fertility inhibition and/or control and also in applications calling for reversible suppression of gonadal activity, such as for the management of precocious puberty or during radiation- or chemo-therapy. They are also useful for treatment of steroid-dependent tumors. Effective dosages will vary with the form of administration and the particular species of mammal being treated. An example of one typical dosage form is a bacteriostatic water solution containing the peptide which solution is administered to provide a dose in the range of about 0.1 to 2.5 mg/kg of body weight. Oral administration of the peptide may be given in either solid form or liquid form.

Results of in vivo testing of selected of the foregoing antagonists are shown in the following Table B:

TABLE B

| Peptide No. | Dosage μg | Rats Ovulating | Dosage μg | Rats Ovulating |
| --- | --- | --- | --- | --- |
| 1. | 50 | 0/7 | 25 | 1/7 |
|  | 10 | 0/10 | 5 | 2/10 |
|  | 2.5 | 9/10 |  |  |
| 3. | 100 | 1/8 | 50 | 2/8 |
| 153. | 500 | 0/7 | 100 | 0/5 |
|  | 25 | 1/11 | 10 | 2/8 |
| 154. | 500 | 0/7 | 100 | 0/7 |
| 156. | 100 | 0/10 | 50 | 0/8 |
|  | 25 | 5/10 |  |  |
| 158. | 500 | 3/5 | 100 | 4/5 |

Although the invention has been described with regard to its preferred embodiments, it should be understood that changes and modifications as would be obvious to one having the ordinary skill in this art may be made without departing from the scope of the invention which is set forth in the claims which are appended hereto. For example, the use of cyclizing bond between the residues in positions 1 and 3 may produce biologically potent peptides without the presence of an accompanying second bond. Other substitutions known in the art which do not significantly detract from the effectiveness of the peptides may be employed in the peptides of the invention. D-2PAL and D-4PAL are considered to be equivalents of D-3PAL. Substituted Phe, such as (4F)Phe, can be used instead of Phe in the 7-position; substituted Phe, such as (2Cl)Phe, can be used instead of Tyr in the 5-position. Other hydrophobic amino acid residues can also be employed in the 1-position, preferably in D-isomer form, and are considered equivalents of those specified.

Particular features of the invention are emphasized in the claims which follow.

What is claimed is:

1. A peptide or a nontoxic salt thereof, said peptide having the formula:

$$X-R_1-(A)D-Phe-R_3-R_4-R_5-R_6-R_7-R_8-(E)Pro-R_{10}-NH_2$$

wherein X is hydrogen or an acyl group having 7 or less carbon atoms; $R_1$ is dehydroPro, D-pGlu, (A)D-Phe, (B)D-Trp, Pro, or β-D-NAL; A is H,Cl, F, NO$_2$, CH$_3$, OCH$_3$, C$^a$Me/4Cl, Cl$_2$ or Br; B is H, NO$_2$, NH$_2$, OCH$_3$, F, Cl, Br, CH$_3$, N$^{in}$For or N$^{in}$Ac; $R_3$ is D-PAL β-D-NAL or (B)D-Trp; $R_4$ is Cys, Asp, Glu, Orn, Dbu, Dpr or Abu; $R_5$ is Glu, Hgl or Hhg; $R_6$ is β-D-NAL, (B)D-Trp, (A')D-Phe, (D)D-Har, D-Tyr, (C)D-His, D-PAL, (D)D-Arg, D-Leu, D-Ile, D-Val, D-Nle, D-Ala, D-Pro, D-Ser(OtBu), or D-Nva; A' is A, NH$_2$, NHCH$_3$ or gua; C is H, imBzl or dinitrophenyl; $R_7$ is Nle, Leu, NML, Phe, Met, Nva, Tyr, Trp or PAL; D is H or di-lower alkyl; $R_8$ is Lys, Hly or Hhl; E is H, OH or dehydro and $R_{10}$ is cys, Asp, Glu, Orn, Dbu, Dpr or Abu; provided however that when $R_4$ is Cys or Abu, $R_{10}$ is Cys or Abu; when $R_4$ is Asp or Glu, $R_{10}$ is Orn, Dbu or Dpr; and when $R_4$ is Orn, Dbu or Dpr, Re is Asp or Glu.

2. A peptide in accordance with claim 1 wherein A is 4Cl or 4F, $R_5$ is Glu and $R_8$ is Lys.

3. A peptide in accordance with claim 2 wherein $R_1$ is β-D-2NAL, $R_3$ is D-PAL and $R_7$ is Leu.

4. A peptide in accordance with claim 3 wherein $R_6$ is D-Trp, D-PAL, β-D-2NAL, (imBzl)D-His or (6NO$_2$)D-Trp.

5. A peptide in accordance with claim 1 wherein $R_4$ is Asp or Glu and $R_{10}$ is Orn, Dbu or Dpr.

6. A peptide in accordance with claim 1 wherein $R_4$ is Orn, Dbu or Dpr and $R_{10}$ is Asp or Glu.

7. A peptide in accordance with claim 1 wherein $R_4$ is Cys and $R_{10}$ is Cys or Abu.

8. A peptide in accordance with claim 1 wherein $R_3$ is (B)D-Trp and B is 6NO$_2$ or N$^{in}$For.

9. A peptide in accordance with claim 8 wherein $R_4$ is Cys or Abu and $R_{10}$ is Cys.

10. A peptide in accordance with claim 1 wherein $R_4$ is Abu and $R_{10}$ is Abu.

11. A peptide in accordance with claim 1 wherein $R_4$ is Asp and $R_{10}$ is Dpr.

12. A peptide in accordance with claim 11 wherein X is Ac, A is 4Cl or 4F and E is H.

13. A peptide in accordance with claim 12 wherein $R_1$ is B-D-2NAL and $R_6$ is D-Arg.

14. A peptide in accordance with claim 13 wherein $R_3$ is D-Trp and $R_7$ is Leu.

15. A peptide in accordance with claim 1 wherein $R_1$ is dehydroPro, $R_3$ is D-PAL, $R_4$ is Glu and $R_{10}$ is Dpr.

16. A peptide in accordance with claim 1 having the formula

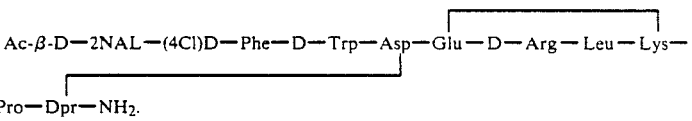

17. A peptide in accordance with claim 1 having the formula

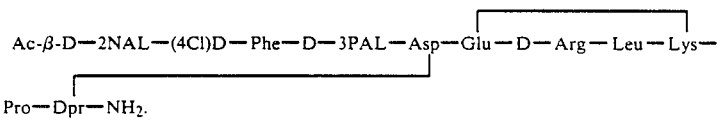

18. A peptide in accordance with claim 1 having the formula

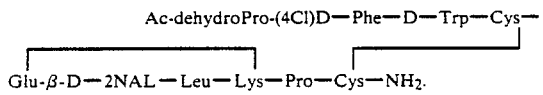

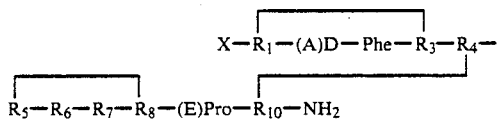

19. A method for regulating the secretion of gonadotropins comprising administering an effective amount of a peptide or a nontoxic salt thereof as defined in claim 1.

20. A peptide or a nontoxic salt thereof, said peptide having the formula:

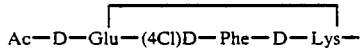

wherein X is hydrogen or an acyl group having 7 or less carbon atoms; R is D-Cys, D-Abu, D-Asp, D-Glu, D-Hgl, D-Hhg, D-Lys, D-Hly, D-Hhl, D-Orn, D-Dbu or D-Dpr; A is H,Cl, F, NO$_2$, CH$_3$, OCH$_3$, C$^a$Me/4Cl, Cl$_2$ or Br; B is H, NO$_2$, NH$_2$, OCH$_3$, F, Cl, Br, CH$_3$, N$^{in}$For or N$^{in}$Ac; R$_3$ is D-Cys, D-Abu, D-Asp, D-Glu, D-Hgl, D-Hhg, D-Lys, D-Hly, D-Hhl, , D-Orn, D-Dbu or D-Dpr; R$_4$ is Cys, Asp, Glu, Orn, Dbu, Dpr or Abu; R$_5$ is Glu, Hgl or Hhg; R$_6$ is β-D-NAL, (B)D-Trp, (A')D-Phe, (D)D-Har, D-Tyr, (C)D-His, D-PAL, (D)D-Arg, D-Leu, D-Ile, D-Val, D-Nle, D-Ala, D-Pro, D-Ser-(OtBu), or D-Nva; A' is A, NH$_2$, NHCH$_3$ or gua; C is H, imBzl or dinitrophenyl; D is H or di-lower alkyl; R$_7$ is Nle, Leu, NML, Phe, Met, Nva, Tyr, Trp or PAL; R$_8$ is Lys, Hly or Hhl; E is H, OH or dehydro and R$_{10}$ is Cys, Asp, Glu, Orn, Dbu, Dpr or Abu; provided however that when R$_4$ is Cys or Abu, R$_{10}$ is Cys or Abu; when R$_4$ is Asp or Glu, R$_{10}$ is Orn, Dbu or Dpr; and when R$_4$ is Orn, Dbu or Dpr, R$_{10}$ is Asp or Glu and provided further that when R$_1$ is D-Cys or D-Abu, R$_3$ is D-Cys or D-Abu; when R$_1$ is D-Asp, D-Glu, D-Hgl or D-Hhg, R$_3$ is D-Lys, D-Hly, D-Hhl, D-Orn, D-Dbu or D-Dpr; and when R$_1$ is D-Lys, D-Hly, D-Hhl, D-Orn, D-Dbu or D-Dpr, R$_3$ is D-Asp, D-Glu, D-Hgl or D-Hhg.

21. A peptide in accordance with claim 20 wherein A is 4Cl or 4F, R$_5$ is Glu, R$_7$ is Leu and R$_8$ is Lys.

22. A peptide in accordance with claim 21 wherein R$_6$ is D-Trp, D-PAL, β-D-2NAL, (imBzl)D-His or (6NO$_2$)D-Trp.

23. A peptide in accordance with claim 20 wherein R$_4$ is Asp or Glu and R$_{10}$ is Orn, Dbu or Dpr.

24. A peptide in accordance with claim 20 wherein R$_4$ is Orn, Dbu or Dpr and R$_{10}$ is Asp or Glu.

25. A peptide in accordance with claim 20 wherein R$_4$ is Cys and R$_{10}$ is Cys or Abu.

26. A peptide in accordance with claim 20 wherein R$_4$ is Asp and R$_{10}$ is Dpr.

27. A peptide in accordance with claim 26 wherein R$_1$ is D-Asp and R$_3$ is D-Lys or D-Orn.

28. A peptide in accordance with claim 26 wherein R$_1$ is D-Cys and R$_3$ is D-Cys.

29. A peptide in accordance with claim 20 having the formula

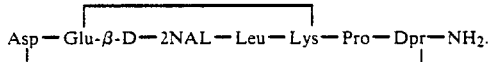

30. A peptide or a nontoxic salt thereof which contains two cyclizing bonds between two of the groups R$_1$ and R$_3$, R$_4$ and R$_{10}$, and R$_5$ and R$_8$, respectively, said peptide having the formula:

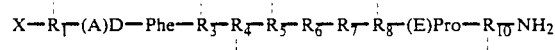

wherein X is hydrogen or an acyl group having 7 or less carbon atoms; R$_1$ is β-D-2NAL, dehydroPro, D-Cys, D-Abu, D-Asp, D-Glu, D-Lys, D-Orn, D-Dbu or D-Dpr; A is H,Cl, F, NO$_2$, CH$_3$, OCH$_3$, C$^a$Me/4Cl, Cl$_2$ or Br; R$_3$ is β-D-2NAL, D-3PAL, D-Trp, D-Cys, D-Abu, D-Asp, D-Glu, D-Lys, D-Orn, D-Dbu or D-Dpr; R$_4$ is Ser, Cys, Asp, Glu, Orn, Dbu, Dpr or Abu; R$_5$ is Tyr, Glu, Hgl or Hhg; R$_6$ is β-D-NAL, (B)D-Trp, (A')D-Phe, (D)D-Har, D-Tyr, (C)D-His, D-PAL, (D)D-Arg, D-Leu, D-Ile, D-Val, D-Nle, D-Ala, D-Pro, D-Ser-(OtBu), or D-Nva; A' is A, NH$_2$, NHCH$_3$ or gua; B is H, NO$_2$, NH$_2$, OCH$_3$, F, Cl, Br, CH$_3$, N$^{in}$For or N$^{in}$Ac; C is H imBzl or dinitrophenyl; D is H or di-lower alkyl; R$_7$ is Nle, Leu, NML, Phe, Met, Nva, Tyr, Trp or PAL; R$_8$ is (D)Arg, (D)Har, Hly, Hhl or Lys; E is H, OH or dehydro; and R$_{10}$ is Gly, D-Ala, Cys, Asp, Glu, Orn, Dbu, Dpr or Abu; provided however that when R$_4$ is Cys or Abu, R$_{10}$ is Cys or Abu; when R$_4$ is Asp or Glu, R$_{10}$ is Orn, Dbu or Dpr; when R$_4$ is Orn, Dbu or Dpr, R$_{10}$ is Asp or Glu; when R$_5$ is Glu, R$_8$ is Lys; when R$_1$ is D-Cys or D-Abu, R$_3$ is D-Cys or D-Abu; when R$_1$ is D-Asp or D-Glu, R$_3$ is D-Lys, D-Orn, D-Dbu or D-Dpr; and when R$_1$ is D-Lys, D-Orn, D-Dbu or D-Dpr, R$_3$ is D-Asp or D-Glu.

31. A peptide or a nontoxic salt thereof which contains a cyclizing bond between R$_1$ and R$_3$ and may contain one or two additional cyclizing bonds between the groups R$_4$ and R$_{10}$, and R$_5$ and R$_8$, respectively, said peptide having the formula

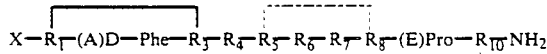

wherein X is hydrogen or an acyl group having 7 or less carbon atoms; R$_1$ is D-Cys, D-Abu, asp, glu, hgl, hhg, lys, hly, hhl, orn, dbu or dpr; A is H,Cl, F, NO$_2$, CH$_3$, OCH$_3$, C$^a$Me/4Cl, Cl$_2$ or Br; R$_3$ is D-Cys, abu, asp, glu, hgl, hhg, lys, hly, hhl, orn, dbu or dpr; R$_4$ is Ser, Cys, Asp, Glu, Orn, Dbu, Dpr or Abu; R$_5$ is Tyr, Glu, Hgl or Hhg; R$_6$ is β-D-NAL, (B)D-Trp, (A')D-Phe, (D)D-Har, D-Tyr, (C)D-His, D-PAL, (D)D-Arg, D-Leu, D-Ile, D-Val, D-Nle, D-Ala, D-Pro, D-Ser(OtBu), or D-Nva; A' is A, NH$_2$, NHCH$_3$ or gua; B is H, NO$_2$, NH$_2$, OCH$_3$, F, Cl, Br, CH$_3$, N$^{in}$For or N$^{in}$Ac; C is H, imBzl or dinitrophenyl; D is H or di-lower alkyl; R$_7$ is Nle, Leu, NML, Phe, Met, Nva, Tyr, Trp or PAL; R$_8$ is (D)Arg, (D)Har, Lys, Hly or Hhl; E is H, OH or dehydro; and R$_{10}$ is Gly, D-Ala, Cys, Asp, Glu, Orn, Dbu, Dpr or Abu; provided however that when R$_4$ is Cys or Abu, it is bonded to R$_{10}$ which is Cys or Abu;

when R$_4$ is Asp or Glu, it is bonded to R$_{10}$ which is Orn, Dbu or Dpr; when R$_4$ is Orn, Dbu or Dpr, it is bonded to R$_{10}$ which is Asp or Glu; when R$_5$ is Glu, Hgl or Hhg, it is bonded to R$_8$ which is Lys, Hly or Hhl; when R$_1$ is D-Cys or D-Abu, it is bonded to R$_3$ which is D-Cys or D-Abu; when R$_1$ is asp, glu, hgl or hhg, it is bonded to R$_3$ which is lys, hly, hhl, orn, dbu or dpr; and when R$_1$ is lys, hly, hhl, orn, dbu or dpr, it is bonded to R$_3$ which is asp, glu, hgl or hhg.

32. A peptide in accordance with claim 31 wherein R$_1$ is D-Glu or D-Hgl and R$_3$ is D-Lys or D-Hly.

33. A peptide in accordance with claim 31 wherein R$_1$ is D-Cys and R$_3$ is D-Cys.

34. A peptide in accordance with claim 31 wherein R$_1$ is D-Abu and R$_3$ is D-Abu.

35. A cyclic peptide or a nontoxic salt thereof which may contain one or two additional cyclizing bonds between two of the groups R$_4$ and R$_{10}$, and R$_5$ and R$_8$, respectively, said peptide having the formula:

wherein X is hydrogen or an acyl group having 7 or less carbon atoms; A is H, Cl, F, NO$_2$, CH$_3$, OCH$_3$, C$^\alpha$-Me/4Cl, Cl$_2$ or Br; n=4 to 11; R$_4$ is Ser, Cys, Asp, Glu, Orn, Dbu, Dpr or Abu; R$_5$ is Tyr, Glu, Hgl or Hhg; R$_6$ is β-D-NAL, (B)D-Trp, (A')D-Phe, (D)D-Har, D-Tyr, (C)D-His, D-PAL, (D)D-Arg, D-Leu, D-Ile, D-Val, D-Nle, D-Ala, D-Pro, D-Ser(OtBu), or D-Nva; A' is A, NH$_2$, NHCH$_3$ or gua; B is H, NO$_2$, NH$_2$, OCH$_3$, F, Cl, Br, CH$_3$, N$^{in}$For or N$^{in}$Ac; C is H, imBzl or dinitrophenyl; D is H or di-lower alkyl; R$_7$ is Nle, Leu, NML, Phe, Met, Nva, Tyr, Trp or PAL; E is H, OH or dehydro; R$_8$ is (D)Arg, (D)Har, Lys, Hly or Hhl and R$_{10}$ is Gly D-Ala Cys Asp Glu Orn Dbu Dpr or Abu; provided however that when R$_4$ is Cys or Abu, it is bonded to R$_{10}$ which is Cys or Abu; when R$_4$ is Asp or Glu, it is bonded to R$_{10}$ which is Orn, Dbu or Dpr; when R$_4$ is Orn, Dbu or Dpr, it is bonded to R$_{10}$ which is Asp or Glu; and when R$_5$ is Glu, Hgl or Hhg, it is bonded to R$_8$ which is Lys, Hly or Hhl.

* * * * *

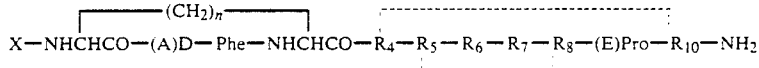

UNITED STATES PATENT AND TRADEMARK OFFICE
CERTIFICATE OF CORRECTION

PATENT NO. : 5,064,939
DATED : 11/12/91
INVENTOR(S) : Rivier, et al.

It is certified that error appears in the above-identified patent and that said Letters Patent is hereby corrected as shown below:

Column 1, line 5, "Grant HD-02903-B" should be --Contract N01-HD-9-2903--; line 12, after "steroids" insert --.-- (period); line 45, after "right" insert --.-- (period); Column 9, line 30, "di nitrophenyl" should be --dinitrophenyl--; Column 10, line 13, "$R^6(X^4$ or $X^5)$" should be --$R_6(X^4$ or $X^5)$--; Column 17, line 45, "(4Br)D-Pre" should be --(4Br)D-Phe--; Column 18, line 25, "VII" should be --VIII--; Column 19, line 49, "D-Glue" should be --D-Glu--; Column 22, line 6, "IN" should be --1N--. Column 24, line 2, after "D-PAL" insert --,-- (comma); line 11, change "cys" to --Cys--; line 14, change "Re" to --$R_{10}$--; Column 25, line 20, "R" should be --$R_1$--; Column 26, line 29, after "H" (first occurrence) insert --,-- (comma); Column 28, lines 12-13, "Gly D-Ala Cys Asp Glu Orn Dbu Dpr" should be --Gly, D-Ala, Cys, Asp, Glu, Orn, Dbu, Dpr--.

Signed and Sealed this

Fourth Day of May, 1993

MICHAEL K. KIRK

*Attest:*

*Attesting Officer*

*Acting Commissioner of Patents and Trademarks*